(12) United States Patent
Sugaya et al.

(10) Patent No.: US 9,254,107 B2
(45) Date of Patent: Feb. 9, 2016

(54) X-RAY CT APPARATUS AND TUBE CURRENT DETERMINATION METHOD

(75) Inventors: Yoshiaki Sugaya, Tokyo (JP); Taiga Goto, Tokyo (JP); Koichi Hirokawa, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 316 days.

(21) Appl. No.: 13/820,539

(22) PCT Filed: Sep. 4, 2011

(86) PCT No.: PCT/JP2011/070079
§ 371 (c)(1),
(2), (4) Date: Mar. 4, 2013

(87) PCT Pub. No.: WO2012/033028
PCT Pub. Date: Mar. 15, 2012

(65) Prior Publication Data
US 2013/0156151 A1 Jun. 20, 2013

(30) Foreign Application Priority Data
Sep. 7, 2010 (JP) .................. 2010-200013

(51) Int. Cl.
*A61B 6/00* (2006.01)
*A61B 6/03* (2006.01)
(52) U.S. Cl.
CPC .............. *A61B 6/032* (2013.01); *A61B 6/405* (2013.01); *A61B 6/542* (2013.01); *A61B 6/544* (2013.01); *A61B 6/545* (2013.01); *A61B 6/4035* (2013.01); *A61B 6/4085* (2013.01); *A61B 6/465* (2013.01); *A61B 6/467* (2013.01)

(58) Field of Classification Search
CPC .......... A61B 6/032; A61B 6/405; A61B 6/48;
A61B 6/481; A61B 6/482; A61B 6/488;
A61B 6/5258; A61B 6/542; A61B 6/544;
A61B 6/545
See application file for complete search history.

(56) References Cited

U.S. PATENT DOCUMENTS 6,067,341 A 5/2000 Horiuchi
6,404,844 B1 * 6/2002 Horiuchi et al. ............... 378/8
(Continued)

FOREIGN PATENT DOCUMENTS

JP 11-104121 4/1999
JP 2001-170037 6/2001
(Continued)

OTHER PUBLICATIONS

International Search Report in PCT/JP2011/070079.

*Primary Examiner* — Thomas R Artman
(74) *Attorney, Agent, or Firm* — Cooper & Dunham LLP

(57) ABSTRACT

In order to provide a technique of obtaining an image having high diagnosability without degrading the operability in an X-ray CT apparatus that suppresses the amount of exposure of an object by controlling the amount of radiation by setting a target image SD and determining the imaging conditions (tube current) satisfying the target image SD, there is provided an X-ray CT apparatus that controls the amount of radiation according to the size of an object in consideration of the contrast by simply inputting one image quality level as a reference of the image quality level that the operator desires. The input image quality level is set as a target image SD when scanning an object having a standard size with a standard tube voltage.

14 Claims, 11 Drawing Sheets

(56) References Cited

U.S. PATENT DOCUMENTS

| | | | |
|---|---|---|---|
| 7,031,423 B2* | 4/2006 | Tsukagoshi | 378/4 |
| 7,106,824 B2* | 9/2006 | Kazama et al. | 378/16 |
| 7,813,471 B2* | 10/2010 | Hirokawa et al. | 378/4 |
| 8,744,039 B2* | 6/2014 | Hirokawa et al. | 378/16 |
| 2004/0032928 A1 | 2/2004 | Toth et al. | |
| 2004/0101105 A1 | 5/2004 | Segawa et al. | |
| 2005/0008115 A1* | 1/2005 | Tsukagoshi | 378/4 |
| 2007/0071172 A1 | 3/2007 | Mollus et al. | |
| 2007/0076842 A1* | 4/2007 | Tkaczyk et al. | 378/5 |
| 2009/0141854 A1* | 6/2009 | Hirokawa et al. | 378/4 |
| 2011/0091008 A1* | 4/2011 | Hirokawa et al. | 378/4 |
| 2013/0156151 A1* | 6/2013 | Sugaya et al. | 378/16 |

FOREIGN PATENT DOCUMENTS

| | | |
|---|---|---|
| JP | 2004-73865 | 3/2004 |
| JP | 2004-173924 | 6/2004 |
| JP | 2007-509687 | 4/2007 |

* cited by examiner

FIG.7

| Set | kV | Ref.SD_kV | Ave. mA | CTDIvol | Rot. Sp | B. Pitch | Thick | Kernel |
|---|---|---|---|---|---|---|---|---|
| ✓ | 80 | 20.3 | 357 | 13.7 | 1.0 | 1.09 | 5 | 32 |
|  | 100 | 13.0 | 293 | 21.3 | 1.0 | 0.84 | 5 | 32 |
|  | 120 | 9.5 | 319 | 36.3 | 1.0 | 1.09 | 5 | 32 |
|  | 140 | 7.3 | 346 | 55.4 | 1.0 | 1.09 | 5 | 32 |

DETERMINE

X-RAY CT APPARATUS AND TUBE CURRENT DETERMINATION METHOD

TECHNICAL FIELD

The present invention relates to an X-ray CT imaging technique. In particular, the present invention relates to a technique of determining the imaging conditions, such as a tube current.

BACKGROUND ART

An X-ray CT apparatus irradiates an object with X-rays from an X-ray tube and collects X-rays, which are detected by an X-ray detector disposed at a position opposite to the X-ray tube and are transmitted through the object, as projection data. In this case, projection data from many directions is collected by rotating the X-ray tube and the X-ray detector opposite each other around the object, and a tomographic image of the object is reconstructed.

The projection data is collected at a position (hereinafter, referred to as a "view") of a discrete X-ray tube. The collected projection data is called projection data at the view. The number of views per one revolution of the X-ray tube that rotates around the object is usually hundreds to thousands. In addition, an operation of collecting projection data of the number of views required to reconstruct one CT image is called a scan.

As a technique for improving the image quality of a reconstructed tomographic image (reconstructed image) while suppressing the amount of exposure of an object, there is a method of determining the tube current value using the image noise standard deviation value (image SD (Standard Deviation)) as an image quality index (for example, refer to PTL 1, PTL 2, and PTL 3). The image SD is a standard deviation of the CT value in the reconstructed image, and is influenced by tube current, the size (X-ray transmission length) of the object, and the like. PTL 1, PTL 2, and PTL 3 disclose the technique of controlling the amount of radiation by setting the target image SD and determining the tube current to realize the target image SD.

By using the technique disclosed in PTL 1, PTL 2, and PTL 3, it is possible to obtain an image that almost satisfies the target image SD. However, the visibility (diagnosability) of the diagnostic target (lesion) within the obtained tomographic image largely depends on the contrast of the image. For example, in a contrast examination using an X-ray CT apparatus, the contrast enhancement effect of tissue (for example, a blood vessel or digestive tract) by a contrast agent enables high-accuracy image diagnosis.

The contrast means an absolute value of the CT value difference between the lesion and the surrounding tissue, for example, and is a different concept from the image SD. Even if the image SD is adjusted to fall within a desired range, desired diagnosability is not necessarily obtained depending on to the size of the contrast. Therefore, there is a technique of determining the imaging conditions taking not only the image SD but also the contrast into consideration (for example, refer to PTL 4). PTL 4 discloses a technique of using a contrast-to-noise ratio (hereinafter, referred to as a "CNR"), which is obtained by dividing the contrast of a diagnostic target and its surroundings by the image SD, as an image quality index. In the technique disclosed in PTL 4, a tube current to achieve the CNR suitable for identifying a diagnostic target is determined on the basis of the size of the diagnostic target input by the operator and the assumed contrast.

CITATION LIST

Patent Literature

[PTL 1] JP-A-2001-043993
[PTL 2] JP-A-2006-055635
[PTL 3] JP-A-2006-116137
[PTL 4] PCT International Publication No. WO2007/138979

SUMMARY OF INVENTION

Technical Problem

As described above, in order to take the contrast variation into consideration in the techniques disclosed in PTL 1, PTL 2, and PTL 3, the operator needs to check the contrast variation himself or herself and reflect it in the target image SD appropriately. However, checking the contrast variation characteristics of an apparatus in advance is a very time-consuming task. In addition, the contrast is influenced by the size of the object and the tube voltage at the time of a scan. Accordingly, it is very difficult for the operator to set the target image SD in consideration of the tube voltage and the object size change whenever the tube voltage at the time of a scan is changed and whenever the object is changed. In addition, since the size of the object varies in the body axis direction even in the same object, it is very difficult for the operator to set the target image SD in consideration of the tube voltage and the object size change. In addition, in the technique disclosed in PTL 4, it is necessary for the operator to input the size of the diagnostic target and the assumed contrast. However, inputting these parameters before imaging is complicated, and the operability is poor.

The present invention has been made in view of the above-described situation, and it is an object of the present invention to provide a technique of obtaining an image having high diagnosability without degrading the operability in an X-ray CT apparatus that suppresses the amount of exposure of an object by controlling the amount of radiation by setting a target image SD and determining the imaging conditions (tube current) satisfying the target image SD.

Solution to Problem

The present invention provides an X-ray CT apparatus that controls the amount of radiation according to the size of an object in consideration of the contrast by simply inputting one image quality level as a reference for the image quality level that the operator desires. The input image quality level is set as a target image SD when scanning an object having a standard size with a specific tube voltage.

Specifically, there is provided an X-ray CT apparatus including an X-ray tube that performs X-ray exposure while rotating around an object, an X-ray detector that is disposed opposite the X-ray tube with the object interposed therebetween and detects the amount of X-rays transmitted through the object, an image reconstruction unit that reconstructs a tomographic image of the object on the basis of the amount of X-rays detected by the X-ray detector, and a display unit that displays the tomographic image. The X-ray CT apparatus includes: a receiving unit that receives an image noise standard deviation, which specific imaging conditions should be within when imaging a standard object having a size set in advance with a specific tube voltage, as a standard image quality level; a scan planning unit that calculates a target image quality level, which is a target image noise standard deviation, using the standard image quality level, calculates a scan tube current to achieve the target image quality level, and sets imaging conditions at the time of actual imaging using the scan tube current; and a control unit that controls operations of the X-ray tube, the X-ray detector, and the image reconstruction unit according to the set imaging conditions.

In addition, there is provided a tube current determination method of determining a scan tube current used in imaging of an X-ray CT apparatus. The tube current determination method includes: an image quality level receiving step of receiving an image noise standard deviation, which specific imaging conditions should be within when imaging a standard object having a size set in advance with a specific tube voltage, as a standard image quality level; a target image quality level calculation step of calculating a target image quality level, which is a target image noise standard deviation, using the standard image quality level; and a tube current determination step of calculating a scan tube current to achieve the calculated target image quality level and determining a tube current, which is used in actual imaging, from the calculated scan tube current.

Advantageous Effects of Invention

According to the present invention, it is possible to obtain an image having high diagnosability without degrading the operability in the X-ray CT apparatus that suppresses the amount of exposure of the object by controlling the amount of radiation by setting the target image SD and determining the imaging conditions (tube current) satisfying the target image SD.

BRIEF DESCRIPTION OF DRAWINGS

FIG. 7 is an explanatory view for explaining another display example of the simultaneous evaluation index display of the second embodiment.

DESCRIPTION OF EMBODIMENTS

First Embodiment

Figure 1:
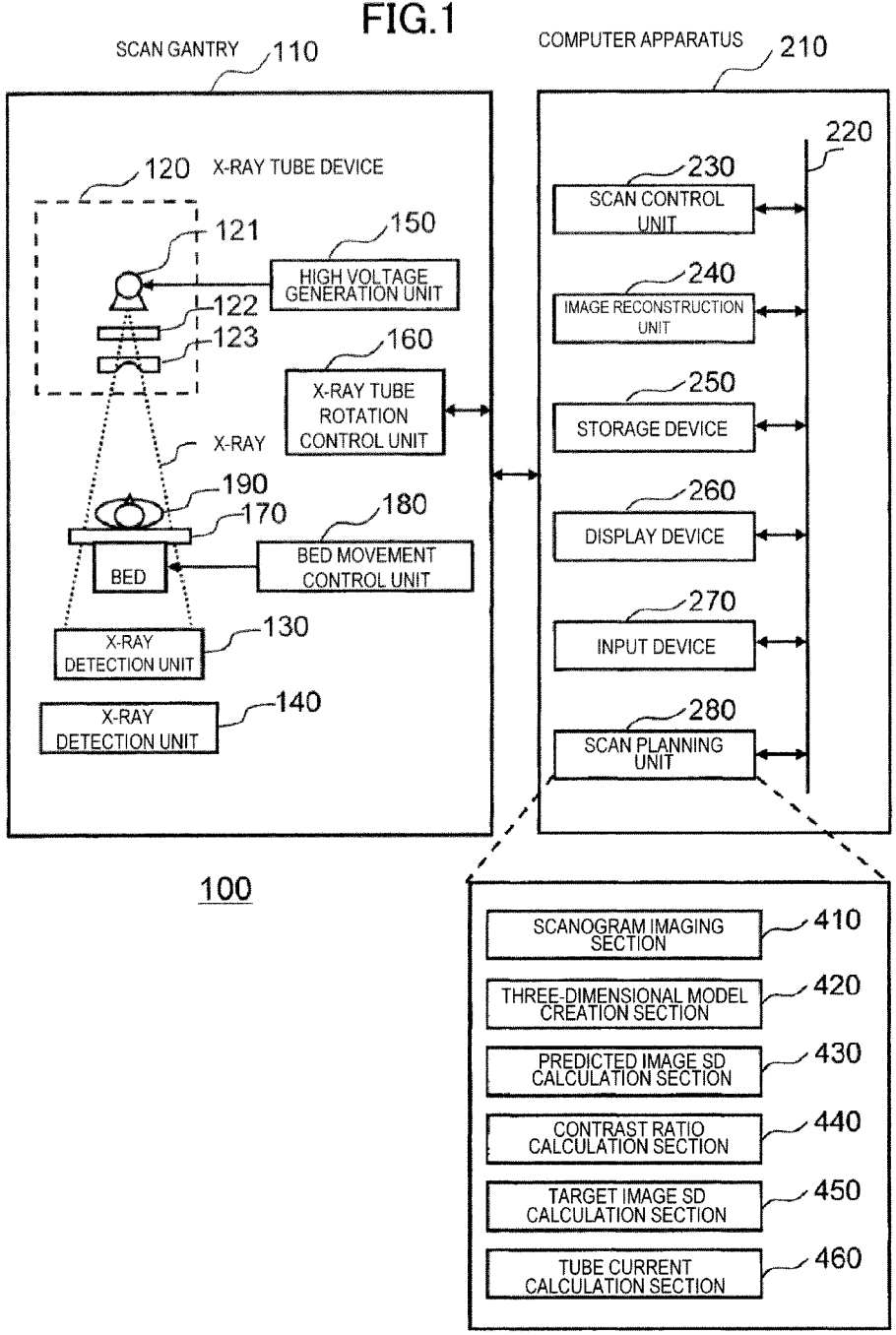
FIG. 1 is a view showing the overall configuration of an X-ray CT apparatus of a first embodiment.

Hereinafter, a first embodiment to which the present invention is applied will be described. Hereinafter, in all drawings for explaining the embodiments of the present invention, the same reference numerals are given to elements having the same functions, and repeated explanation thereof will be omitted.

First, an X-ray CT apparatus of the present embodiment will be described. The X-ray CT apparatus includes an X-ray tube that irradiates an object with X-rays and an X-ray detector that detects X-rays transmitted through the object. The detected X-rays are output as projection data. This is an apparatus that collects projection data from many directions by rotating the X-ray tube and X-ray detector opposite each other around the object and reconstructs a tomographic image of the object by back-projection.

Examples of the X-ray CT apparatus include a single slice type X-ray CT apparatus to obtain one tomographic image by the single X-ray exposure and a multi-slice type X-ray CT apparatus to obtain a plurality of tomographic images by the single X-ray exposure. In the single slice type X-ray CT apparatus, a fan beam (fan-shaped beam) is irradiated from the X-ray tube, and X-rays transmitted through the object are measured by the X-ray detector in which a number of X-ray detection elements are arrayed in a column, that is, in a one-dimensional direction (channel direction), thereby obtaining the projection data of the object. In the multi-slice type X-ray CT apparatus, a cone beam (a conical or pyramid-shaped beam) is irradiated from the X-ray tube, and X-rays transmitted through the object are measured by the X-ray detector in which a number of X-ray detection elements are arrayed in a two-dimensional direction (a channel direction and a column direction), hereby obtaining the projection data of the object. The projection data corresponding to one view includes data corresponding to the number of channels×the number of columns of the X-ray detector (in the case of a single slice type X-ray CT apparatus, the number of columns is 1).

An axial scan, a spiral scan, and the like are known as methods of a scan. In addition, there are a single radiation source type in which there is one X-ray source and a multi-radiation source type in which there are many X-ray sources.

In the X-ray CT apparatus of the present embodiment, imaging conditions in which not only the image SD but also contrast variation in the object is considered are determined according to the image quality level specified by the operator before the start of a scan, and the scan is performed in the determined imaging conditions. Although the present embodiment can be applied regardless of the scanning method (an axial scan and a spiral scan), the slice type (a single slice type and a multi-slice type), and the number of radiation sources (a single radiation source type and a multi-radiation source type), a case where the present embodiment is applied to a single radiation source type and a multi-slice spiral scan type X-ray CT apparatus will be described as an example.

FIG. 1 is a view showing the overall configuration of an X-ray CT apparatus of the present embodiment. As shown in this drawing, an X-ray CT apparatus 100 of the present embodiment includes a scan gantry 110 and a computer apparatus 210. The scan gantry 110 irradiates an object 190 with X-rays and collects projection data of the X-rays transmitted through the object 190. The computer apparatus 210 performs various kinds of data processing, such as controlling the overall operation of the X-ray CT apparatus 100 to execute various scans and performing reconstruction processing of a CT image using the projection data collected by the scan gantry 110.

The scan gantry 110 includes an X-ray tube device 120, an X-ray detection unit 130, a data collection unit 140, a high voltage generation unit 150, an X-ray tube rotation control unit 160, a bed 170, and a bed movement control unit 180.

The X-ray tube device 120 includes an X-ray tube 121, an X-ray filter 122, and a compensation filter 123. The X-ray tube 121 is an X-ray source, and irradiates the object 190 with X-rays using electrical power supplied from the high voltage generation unit 150. The X-ray filter 122 and the compensation filter 123 are provided to reduce the amount of exposure of the object 190 and maintain the intensity of X-rays transmitted through the object constant.

The X-ray detection unit 130 is disposed opposite the X-ray tube device 120, and detects X-rays transmitted through the object 190. The X-ray detection unit 130 includes a plurality of X-ray detection elements, and detects X-rays incident on these X-ray detection elements and outputs an electrical signal corresponding to the strength of the detected X-rays. These X-ray detection elements are arrayed by about 1000 channels in the circumferential direction of the X-ray tube 121 and by 1 to 500 channels in the body axis direction of the object 190, for example.

The data collection unit 140 collects the electrical signal output from the X-ray detection unit 130 and transmits it to the computer apparatus 210 as projection data.

The high voltage generation unit 150 performs control, such as the adjustment of the amount of irradiated X-rays, by adjusting electrical power supplied to the X-ray tube 121. In addition, the high voltage generation unit 150 includes a high voltage transformer, a filament current generator, and a rectifier, and further includes a tube voltage switcher and a filament current switcher for adjusting a tube voltage and a filament current arbitrarily or gradually.

In addition, the X-ray tube device 120, the X-ray detection unit 130, and the data collection unit 140 are mounted in a manner facing an annular rotating frame (rotating disc) which are not shown in FIG. 1. The rotating frame is driven and rotated by the X-ray tube rotation control unit 160. Accordingly, the X-ray tube device 120, the X-ray detection unit 130, and the data collection unit 140 rotate around the object 190.

The object 190 is placed on the bed 170. The bed 170 is driven by the bed movement control unit 180 to insert the object 190 into the imaging port of the scan gantry 110 in synchronization with the irradiation of X-rays.

The computer apparatus 210 includes a scan control unit 230, an image reconstruction unit 240, a storage device 250, a display device 260, an input device 270, and a scan planning unit 280. In the computer apparatus 210, these units are connected to each other through a bus 220.

The computer apparatus 210 includes a CPU, a memory, and a storage device, and each function of the computer apparatus 210 is realized when the CPU loads a program stored in the storage device in advance to the memory and executes the program.

The scan control unit 230 controls each unit of the scan gantry 110 according to the imaging conditions set by the scan planning unit 280, and executes a scan. For example, according to the scan tube current set as an imaging condition, the scan control unit 230 controls the high voltage generation unit 150 to execute a scan while adjusting the output of X-rays.

The image reconstruction unit 240 receives data (projection data) transmitted from the scan gantry 110 and processes the data to reconstruct a tomographic image of the object. In this manner, a tomographic image of the object 190 based on the amount of X-rays after transmission detected by the X-ray detection unit 130 is obtained. The tomographic image reconstructed by the image reconstruction unit 240 is transmitted to the display device 260 through the bus 220, and is displayed on a monitor provided in the display device 260, which will be described later. In addition, in the present embodiment, an operation until a scan is performed to reconstruct a tomographic image (CT image) is called imaging.

The input device 270 includes a mouse and a keyboard, for example, and receives various inputs from the operator of the X-ray CT apparatus 100. In the present embodiment, for example, inputs of various kinds of setting values, such as the image quality level and the imaging conditions, instructions to start various kinds of processing, and the like are received.

The storage device 250 stores the various setting values received from the operator through the input device 270, the imaging conditions calculated by the scan planning unit 280, the tomographic image reconstructed by the image reconstruction unit 240, and the like. In addition, data obtained during the processing of each unit is temporarily stored.

The display device 260 includes a monitor, for example, and displays the tomographic image reconstructed by the image reconstruction unit 240, the imaging conditions calculated by the scan planning unit 280, and the like for the operator. In addition, data obtained by the processing of each unit is displayed when necessary so as to be presented to operator.

The scan planning unit 280 calculates parameters, which are required for the execution of imaging to obtain a CT image used in diagnosis (hereinafter, referred to as actual imaging), from the parameters input through the input device 270 by the operator, and performs an imaging preparation process for setting the imaging conditions, in the imaging preparation process of the present embodiment, for example, inputs such as a tube voltage (scan tube voltage) used in the sequence of actual imaging, a range (scan range) in which actual imaging is performed, a slice thickness at the time of actual imaging, an image quality level as a reference, and information specifying an object with a standard size which will be described later, are received, and a tube current (scan tube current) at the time of actual imaging is calculated.

In the present embodiment, an image SD (hereinafter, referred to as a standard reference SD), which is an upper limit when imaging an object (standard object) having a standard size with the standard tube voltage set in advance, is used as the image quality level as a reference. In addition, the imaging conditions in which the standard object is photographed with the standard tube voltage are called standard conditions. This standard tube voltage is set in advance at the time of protocol setting, and is stored in the storage device 250. In addition, the information (standard object model) that specifies the standard object is also input in advance, and is stored in the storage device 250. In the present embodiment, long and short axes of the water-equivalent ellipse are registered as a standard object model.

In order to execute the imaging preparation process, the scan planning unit 280 of the present embodiment includes a scanogram imaging section 410, a three-dimensional model creation section 420, a predicted image SD calculation section 430, a contrast ratio calculation section 440, a target image SD calculation section 450, and a tube current calculation section 460.

The scanogram imaging section 410 executes scanogram imaging of the object 190 to obtain scanogram data and a scanogram image. The scanogram image acquisition procedure is basically the same as the procedure of obtaining a CT image in actual imaging. According to the imaging sequence set in advance, the scanogram imaging section 410 gives an instruction to each unit of the scan gantry 110 to operate each unit of the scan gantry 110, and makes the data collection unit 140 collect projection data. The projection data collected at this time is scanogram data. Here, in scanogram imaging, the scanogram data is collected by irradiating the object 190 with X-rays from the fixed direction, for example, from the back surface direction without rotating the X-ray tube 121.

The collected scanogram data is transmitted from the data collection unit 140 to the image reconstruction unit 240, and is used for the creation of a scanogram image. The generated scanogram image is used for the setting of a scan range and a slice position (CT image reconstruction position) setting at the time of a scan, for example.

In addition, in the present embodiment, the collected scanogram data is also used for the creation of a three-dimensional object model, which will be described later.

The three-dimensional model creation section 420 creates a three-dimensional model of the object (three-dimensional object model) by analyzing the scanogram data. The scan range received from the operator is set as a range in the three-dimensional object model created by analyzing the scanogram data. For example, the three-dimensional object model is obtained by approximating each cross-section of the object 190, which corresponds to the arbitrary position (Z position) along the body axis direction of the object 190, to the elliptical cross-section (water-equivalent ellipse) having an X-ray absorption coefficient equivalent to water. This model is a three-dimensional model in which the lengths of the long and short axes change according to the Z position of the object 190. Data of the created three-dimensional object model is stored in the storage device 250. In addition, when the data of the size of each slice position of the object is stored, this function may not be included.

The predicted image SD calculation section 430 calculates a predicted value (predicted image SD; SD(Z)_pred) of the image SD of the Z position corresponding to each slice position. The calculated predicted image SD (SD(Z)_pred) is used to calculate a scan tube current which will be described later. The predicted image SD (SD(Z)_pred) is calculated using the method disclosed in PTL 3 and the like. Specifically, the X-ray transmission length of the object at the Z position corresponding to each slice position is calculated, and the predicted image SD (SD(Z)_pred) is calculated using the correlation between the image SD and the tube current (the image SD is proportional to the inverse of the square root of the tube current) according to the X-ray transmission length. This correlation between the image SD and the tube current is determined from data, which is obtained by performing imaging at the standard tube current using water phantoms with various sizes, using the X-ray CT apparatus 100 to be used, for example. Alternatively, the correlation between the image SD and the tube current is created on the basis of simulation data.

In addition, the X-ray transmission length WT of the Z position (slice position Z) corresponding to each slice position is calculated from the three-dimensional object model. That is, a diameter of the elliptical cross-section of the three-dimensional object model at each slice position Z, which is based on the rotation angle from the reference position of the rotating frame, is calculated as the X-ray transmission length WT. Therefore, the calculated X-ray transmission length WT is expressed, for example, as a function of the slice position Z and the rotation angle θ from the reference position of the rotating frame using the long-axis length (WDia_X(Z)) and the short-axis length (WDia_Y(Z)) of the elliptical cross-section of the three-dimensional object model at each slice position Z (WT(Z, θ)).

The contrast ratio calculation section 440 calculates the contrast ratio at each slice position Z. The contrast ratio is obtained by standardizing the contrast when imaging the object, which has a size corresponding to the slice position Z, with the scan tube voltage, using the contrast obtained by imaging in the standard conditions.

Here, a water equivalent diameter (WDia(Z)) that is calculated according to the following expression (1) using the long-axis length (WDia_X(Z)) and the short-axis length (WDia_Y(Z)) of the elliptical cross-section of the three-dimensional object model at each slice position Z is used as the object size corresponding to the slice position Z.

[Expression 1]

$$WDia(Z) = \sqrt{WDia\_X(Z) * WDia\_Y(Z)} \quad (1)$$

Figure 2:
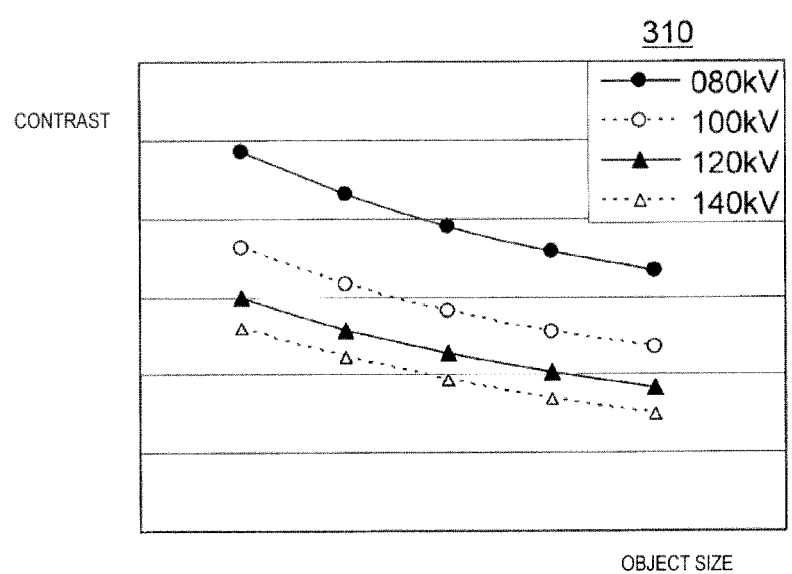
FIG. 2 is a graph of the contrast variation curves of the first embodiment.

The contrast at each slice position is determined using the contrast variation curve for each tube voltage. FIG. 2 shows an example of a contrast variation curve 310 for each tube voltage. The contrast variation curve 310 is a graph showing the relationship between the object size (WDia(Z)) and the contrast at a predetermined tube voltage. This contrast variation curve 310 is measured for each tube voltage, which can be set in the X-ray CT apparatus 100, using a phantom or the like in advance and is stored in the storage device 250.

For example, the measurement is performed using a water rod which is inserted into a cylindrical water phantom and contains a contrast agent solution. For each tube voltage, the radius of the water rod in which the contrast agent solution is contained is fixed and the radius of the water phantom is changed, thereby allowing measurement of the contrast variation.

As shown in FIG. 2, the object size is associated with the beam hardening effect. As the object size decreases, the beam hardening effect decreases, and the contrast is improved. In addition, in general, since the X-ray absorption capability increases as the X-ray energy decreases, the contrast is improved as the tube voltage decreases.

In addition, the influence on the contrast differs depending on whether or not there is an X-ray filter. Therefore, it is preferable to measure the relationship between the object size and the contrast according to the type of the X-ray filter and store this additionally. In addition, the main component of the contrast agent that is currently used in the X-ray CT apparatus 100 is iodine. For this reason, contrast variation in the iodine contrast agent is assumed in FIG. 2. In the case of a contrast agent having main components other than iodine, the change of the contrast variation characteristics may be considered. Therefore, a configuration is also possible in which the relationship between the object size and the contrast is measured according to the type of main components of the contrast agent to be used and the measured relationship is stored. In this case, means for inputting the main component of the contrast agent used at the time of actual imaging is provided, and the contrast variation curve 310 corresponding to the registered main component is read and used.

Using the contrast variation curve 310 shown in FIG. 2, the contrast ratio calculation section 440 obtains the contrast (Cnt(Z)_kV), which corresponds to the object size (WDia(Z) of the position, at each slice position Z on the graph of the scan tube voltage.

The contrast ratio calculation section 440 similarly obtains the contrast (Cnt(std)_kVptcl), which is obtained in the standard conditions. That is, using the long-axis length and the short-axis length of the standard object model registered in advance, the water-equivalent diameter of the standard object is calculated as the standard object size (WDia(std)) using the above-described expression (1). In addition, the contrast (Cnt (std)_kVptcl) corresponding to the standard object size (WDia(std)) is obtained on the graph of the standard tube voltage.

Using these, the contrast ratio calculation section 440 calculates a contrast ratio (Cnt_Ratio(Z)_kV) according to the following expression (2).

[Expression 2]

$$\text{Cnt\_Ratio}(Z)\_kV = \frac{Cnt(Z)\_kV}{Cnt(std)\_kVptcl} \quad (2)$$

The target image SD calculation section 450 calculates a target image SD (tgt_SD(Z)) of each slice position Z at the scan tube voltage. The target image SD is obtained by multiplying the contrast ratio (Cnt_Ratio(Z)_kV) at each slice position Z by the standard reference SD (Ref. SD_kVptcl). Here, the target image SD is calculated according to the following expression (3).

[Expression 3]

$$\text{tgt\_SD}(Z) = \text{Ref.SD\_kVptcl} * \text{Cnt\_Ratio}(Z)\_kV * k(\text{Cnt\_Ratio}(Z)\_kV) \quad (3)$$

Here, the standard reference SD (Ref. SD_kVptcl) is a target image SD when performing imaging in the standard conditions, and is input as an image quality level as a reference in advance through the input device 270 from the operator. In addition, k(Cnt_Ratio(Z)_kV) is a proportionality constant that depends on the contrast ratio (Cnt_Ratio(Z)_kV).

In addition, the proportionality constant k(Cnt_Ratio(Z)_kV) is determined in consideration of human visual characteristic change that changes according to changes in the contrast of an object to be identified. Specifically, the proportionality constant k(Cnt_Ratio(Z)_kV) is calculated by performing reading and experiments for a plurality of objects with different contrasts in advance to check the change in the identification capability in advance. For example, the proportionality constant k(Cnt_Ratio(Z)_kV) is calculated according to the following expression (4).

[Expression 4]

$$k(\text{Cnt\_Ratio}(Z)\_kV) = c + d * \text{Cnt\_Ratio}(Z)\_kV \quad (4)$$

Here, c and d are real constants. In addition, the expression (4) is a linear equation. The determined proportionality constant k(Cnt_Ratio(Z)_kV) is stored in the storage device 250 in advance. In addition, the calculation of the proportionality constant k(Cnt_Ratio(Z)_kV) is not limited to this.

The tube current calculation section 460 calculates a scan tube current, which satisfies the target image SD (tgt_SD(Z)), using the predicted image SD (SD(Z)_pred) and the target image SD (tgt_SD(Z)) at each slice position Z. Specifically, the scan tube current can be calculated using the same method as the method disclosed in PTL 3.

Figure 3:
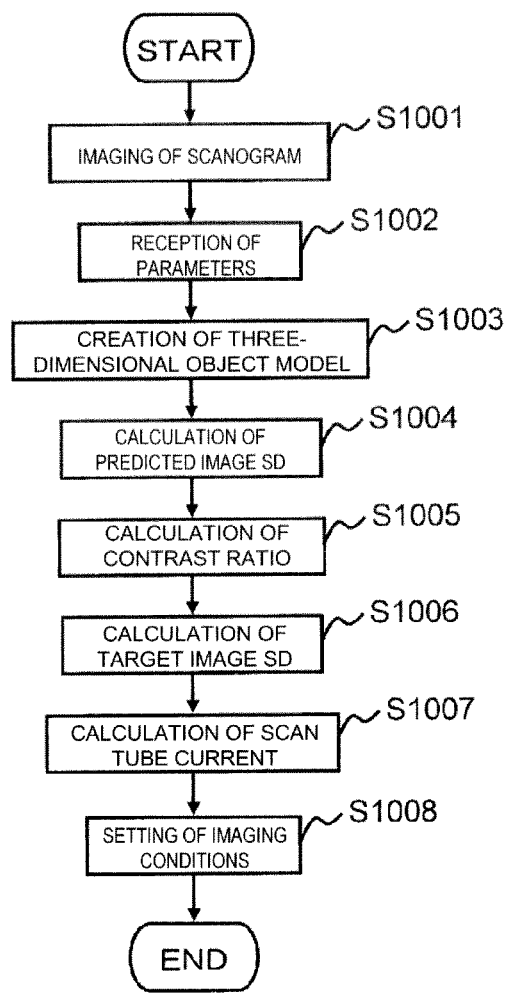
FIG. 3 is a flow chart of the imaging preparation process of the first embodiment.

Next, the flow of the imaging preparation process by the scan planning unit 280 of the present embodiment using each unit described above will be described. FIG. 3 is a process flow of the imaging preparation process of the present embodiment. The scan planning unit 280 starts the imaging preparation process in response to an instruction to start the imaging preparation process from the operator.

In addition, the standard tube voltage and the standard object model are stored in the storage device 250 in advance.

First, the scanogram imaging section 410 executes scanogram imaging to obtain scanogram data and a scanogram image (step S1001).

Then, the scan planning unit 280 receives the setting of various parameters through the input device 270 (step S1002). Here, inputs of the scan range (that is, a scan start position and a scan end position), scan tube voltage, scan time, X-ray collimation conditions, image slice thickness, type of a reconstruction filter function, field-of-view size, image quality level (standard reference SD), and the like are received. The scan range is received on the scanogram image displayed on the display device 260. In addition, the scan start position and the scan end position mean the Z position of the first CT image obtained by a series of scans and the Z position of the last CT image, respectively.

Then, the three-dimensional model creation section 420 creates a three-dimensional object model (step S1003). Here, the Z position (slice position Z) corresponding to each slice position is determined from the scan range and the image slice thickness input in step S1002, for example. Then, scanogram data within the scan range is analyzed, and the water-equivalent ellipse at each slice position Z is determined.

Then, the predicted image SD calculation section 430 calculates the predicted image SD (SD(Z)_pred) at each slice position Z (step S1004). In addition, the timing of this process is not limited if it is before the calculation of the scan tube current, which will be described later, after the determination of the slice position Z.

Then, the contrast ratio calculation section 440 calculates the contrast ratio (Cnt Patio(Z)_kV) at each slice position Z at the scan tube voltage (step S1005). As described above, the contrast ratio is calculated from the contrast (Cnt(Z)_kV) at each slice position Z, which is calculated using the contrast variation curve 310 for each tube voltage, and the contrast in the standard conditions.

Then, the target image SD calculation section 450 calculates the target image SD (tgt_SD(Z)) using the contrast ratio (Cnt_Ratio(Z)_kV) and the standard reference SD (Ref. SD_kVptcl) (step S1006).

Then, the tube current calculation section 460 calculates a scan tube current i(Z) at each slice position Z using the predicted image SD (SD(Z)_pred) and the target image SD (tgt_SD(Z) (step S1007).

The scan planning unit 280 sets the scan tube current calculated through the above procedure and the scar parameters received in step S1002 as imaging conditions (step S1008), and ends the imaging preparation process.

As described above, according to the present embodiment, the input of the standard reference SD (Ref. SD_kVptcl), which is the target image SD in the standard conditions, is received as a target image quality level before performing actual imaging in the X-ray CT apparatus 100. Then, the target image SD (tgt_SD(Z)) at each slice position Z is calculated using the standard reference SD (Ref. SD_kVptcl), and the scan tube current is determined.

The contrast ratio is used for the calculation of the target image SD (tgt_SD(Z)). For this reason, the target image SD (tgt_SD(Z)) calculated for each slice position Z is obtained in consideration of the contrast. Accordingly, a CT image obtained by the determined scan tube current has high diagnosability.

In addition, the operator inputs the target image SD in the standard conditions. Therefore, the operability of the control of the amount of radiation in the X-ray CT apparatus of the present embodiment is almost similar to that in an X-ray CT apparatus in the related art in which the amount of radiation is controlled by setting the target image SD and determining the tube current. Therefore, the X-ray CT apparatus of the present embodiment can be used without having an adverse effect on the operability.

In addition, for the target image SD in which the contrast has been taken into consideration, the size of the object is also taken into consideration. As shown in FIG. 2, as the size of the object decreases, the contrast increases.

According to the present embodiment, when the size of the object is smaller than the standard object size, the target image SD is set to be larger than the input standard reference SD (Ref. SD_kVptcl) from the expression (3). Therefore, it is possible to ensure the same image quality by further suppressing the amount of exposure. Therefore, according to the present embodiment, the amount of exposure can be optimized according to the size of the object in consideration of the contrast of a CT image.

In addition, for the target image SD in which the contrast has been taken into consideration, the tube voltage is also taken into consideration. As show n FIG. 2, in the case of the size of the same object, the contrast increases as the tube voltage decreases. Accordingly, when the size of the object is the same, the target image SD can be set to be larger than Ref. SD_kVptcl by using the tube voltage lower than the standard tube voltage. Therefore, a scan that ensures the same image quality while suppressing the amount of exposure is possible.

As described above, according to the present embodiment, in the X-ray CT apparatus that suppresses the amount of exposure of the object by controlling the amount of radiation by setting the target image SD and determining the scan tube current, it is possible to obtain an image having high diagnosability without degrading the operability.

In addition, although the long-axis length and the short-axis length of the water-equivalent elliptical cross-section are registered in advance as the information specifying the standard object in the above-described embodiment, the present invention is not limited thereto. For example, the water-equivalent diameter (WDia) may be calculated from the standard body weight (Wgt_Std) of the object or the standard cross-sectional area of the object.

The water-equivalent diameter (WDia) is calculated from the standard body weight (Wgt_Std) using the following expression (5)

[Expression 5]

$$WDia = a + b * Wgt\_std \quad (5)$$

Here, a and b are real constants. As a and b, different values may be stored for each part in a scan range. The standard body weight (Wgt_Std) may be stored in advance, or may be calculated from the object information (national origin, age, sex, height, weight) stored in the storage device 250, for example.

In addition, an equation for conversion from the standard body weight (Wgt_Std) to the water-equivalent diameter (WDia) is not limited to the linear conversion such as expression (5). As long as conversion error from the standard body weight to the water-equivalent diameter is small, any kind of equation for conversion may be used. In addition, the standard body weight is stored in the storage device 250 in advance. In this case, it is preferable to store standard body weights every conditions of significantly different values, such as "adult object" and "child object". In addition, also for the "adult object", the standard body weight may be stored as a table according to sex or country.

In addition, in the present embodiment, the standard reference SD (Ref. SD_kVptcl) which is the target image SD in the standard conditions is used as an image quality level that the operator inputs and specifies. However, the image quality level specified by the operator is not limited to this. For example, it is also possible to use an image SD (reference SD; Ref. SD_kV) that is an upper limit when imaging the standard object with the scan tube voltage.

In this case, the target image SD calculation section 430 calculates the target image SD (tgt_SD(Z)) at each slice position Z using the following expression (6).

[Expression 6]

$$tgt\_SD(Z) = Ref.SD\_kV * Cnt\_Ratio(Z)\_kV * k(Cnt\_Ratio(Z)\_kV) \quad (6)$$

In this case, the contrast ratio calculation section 440 calculates the contrast ratio (Cnt_Ratio(Z)_kV) according to the following expression (7).

[Expression 7]

$$Cnt\_Ratio(Z)\_kV = \frac{Cnt(Z)\_kV}{Cnt(std)\_kV} \quad (7)$$

That is, the contrast (Cnt (Z)_kV) at each slice position Z at the scan tube voltage is standardized using the contrast Cnt (std)_kV when imaging the standard object with the scan tube voltage. In addition, the proportionality constant k(Cnt_Ratio (Z)) is calculated in the same manner as in the above-described expression (4).

The flow of the imaging preparation process when the image quality level specified by the operator is set as the reference SD (Ref. SD_kV) is basically the same as the process flow shown in FIG. 3. Here, the image quality level that the operator inputs in step S1002 is a reference SD (Ref. SD_kV) In addition, as shown in the above-described expressions (5) and (6), the calculation of the contrast ratio in step S1005 is performed on the basis of the contrast variation curve 310 at the scan tube voltage in FIG. 2.

Through such a configuration, the parameter that the operator inputs as an image quality level becomes a target image SD that is an upper limit when imaging the standard object with the scan tube voltage. Therefore, since a difference between the image SD of the obtained tomographic image and the input value is reduced, it becomes easy for the operator to check the image quality in advance.

As described above, according to the present embodiment, in the X-ray CT apparatus that controls the amount of radiation by setting the target image SD, the amount of radiation for imaging can be determined by appropriately taking contrast variation into consideration. That is, according to the present embodiment, the imaging conditions are calculated in consideration of not only the image SD but also the contrast variation of the object, and a scan is performed in the calculated imaging conditions. Therefore, it is possible to provide an X-ray CT apparatus that obtains a tomographic image with sufficient quality required for diagnosis while preventing excessive X-ray exposure.

Second Embodiment

Next, a second embodiment to which the present invention is applied will be described. An X-ray CT apparatus of the present embodiment has basically the same configuration as that in the first embodiment. In addition, also in the present embodiment, the imaging conditions are determined by calculating the tube current on the basis of the image quality level input by the operator in the same procedure as in the first embodiment. In the present embodiment, however, an operator's change of the tube current calculated in the procedure of the first embodiment is received. Therefore, a computer apparatus 210 of the present embodiment includes a scan planning unit 281 instead of the scan planning unit 280 of the first embodiment. Hereinafter, the present embodiment will be described focusing on the different configuration from the first embodiment.

Figure 4:
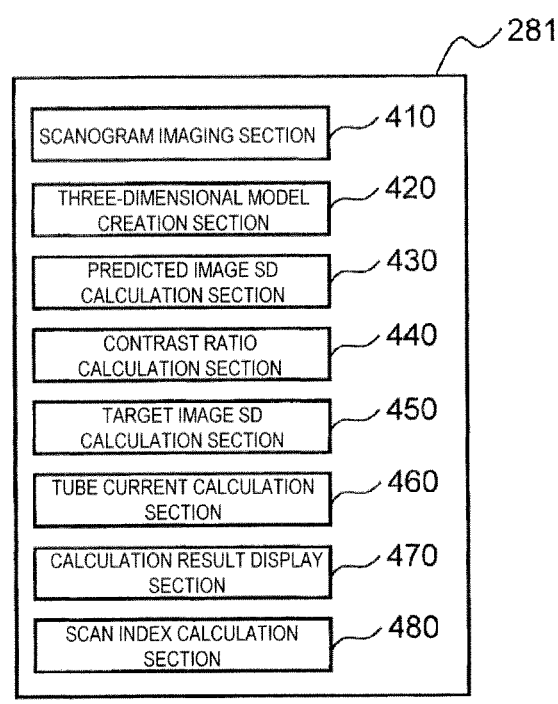
FIG. 4 is a functional block diagram of a scan planning unit of a second embodiment.

FIG. 4 shows a functional block of the scan planning unit 281 of the present embodiment. As shown in this drawing, the scan planning unit 281 of the present embodiment executes an imaging preparation process as in the first embodiment.

Accordingly, the scan planning unit 281 includes a scanogram imaging section 410, a three-dimensional model creation section 420, a predicted image SD calculation section 430, a contrast ratio calculation section 440, a target image SD calculation section 450, and a tube current calculation section 460.

In addition, the scan planning unit 281 of the present embodiment receives an operator's instruction to approve and/or change results calculated by the target image SD calculation section 450 and the tube current calculation section 460. In order to realize this, the scan planning unit 281 of the present embodiment further includes a calculation result display section 470 and a scan index calculation section 480.

After the tube current calculation section 460 calculates the scan tube current, the scan index calculation section 480 calculates a reference SD (Ref. SD_kV) at scan tube voltage (kV), average tube current (Ave.mA), and the amount of exposure (CTDIvol) as scan condition evaluation indices. In addition, the average tube current is an average value of scan ube current modulated in the scan range. In addition, the scan index calculation section 480 calculates the above-described scan condition evaluation index for each tube voltage, which can be set in the X-ray CT apparatus 100, according to the instruction from the operator.

Since the reference SD (Ref. SD_kV) at each tube voltage (kV) is a target image SD that is an upper limit when imaging the standard object with scan tube voltage (kV), the reference SD (Ref. SD_kV) at each tube voltage (kV) is calculated as in the following expression (8) from the expression (3) of the first embodiment.

[Expression 8]

$$\text{Ref.SD\_kV} = \text{Ref.SD\_kVptcl} * \text{Cnt\_Ratio(std)\_kV} * k(\text{Cnt\_Ratio(std)\_kV}) \quad (8)$$

Here, Cnt_Ratio(std)_kV is a contrast ratio obtained by standardizing the contrast of the standard object at each tube voltage using the contrast Cnt(std)_kVptcl of the standard object at the standard tube voltage, and is calculated by the following expression (9).

[Expression 9]

$$\text{Cnt\_Ratio}(std)\_kV = \frac{\text{Cnt}(std)\_kV}{\text{Cnt}(std)\_kVptcl} \quad (9)$$

In addition, k(Cnt_Ratio(std)_kV) is a proportionality constant that depends on the contrast ratio (Cnt_Ratio(std)_kV). This proportionality constant k(Cnt_Ratio(std)_kV) is determined in consideration of human visual characteristic change that changes according to changes in the contrast of an object to be identified, and is calculated according to the following expression (10), for example.

[Expression 10]

$$k(\text{Cnt\_Ratio}(std)\_kV) = c + d * \text{Cnt\_Ratio}(std)\_kV \quad (10)$$

Here, c and d are real constants.

In addition, a tube current at the tube voltage other than the scan tube voltage is calculated using the calculated reference SD (Ref. SD_kV) and the method of the first embodiment. In addition, the average tube current (Ave. mA) and the amount of exposure (CTDIvol) are calculated from the calculated tube current.

In addition, when a change of the value of the reference SD (Ref. SD_kV) is received from the operator, the scan index calculation section 480 of the present embodiment calculates the reference SD of other tube voltages using the value of the changed reference SD (Ref. SD_kV) as a standard reference SD (Ref. SD_kVptcl) and the tube voltage corresponding to the changed reference SD as a standard tube voltage.

The calculation result display section 470 displays a calculation result of the scan index calculation section 480 on the display device 260.

Figure 5:
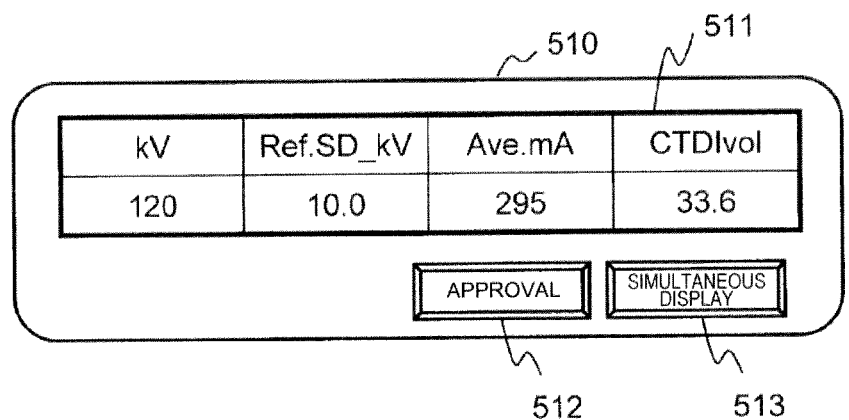
FIG. 5 is an explanatory view for explaining a display example of evaluation index display of the second embodiment.

When the scan index calculation section 480 calculates a scan condition evaluation index at the scan tube voltage (kV), the calculation result display section 470 generates an evaluation index display 510 using the calculated scan condition evaluation index and displays it on the display device 260. FIG. 5 shows a display example of the evaluation index display 510. As shown in this drawing, the evaluation index display 510 includes a scan condition evaluation index 511, an approval button 512, and a simultaneous display button 513.

The approval button 512 receives an instruction to set the displayed scan condition evaluation indices as the imaging conditions of actual imaging. On the other hand, the simultaneous display button 513 receives an instruction to change the imaging conditions with reference to other imaging conditions. When an instruction according to the pressing of the simultaneous display button 513 is received, the scan index calculation section 480 calculates the above-described scan condition evaluation index for each tube voltage that can be set in the X-ray CT apparatus 100.

Figure 6:
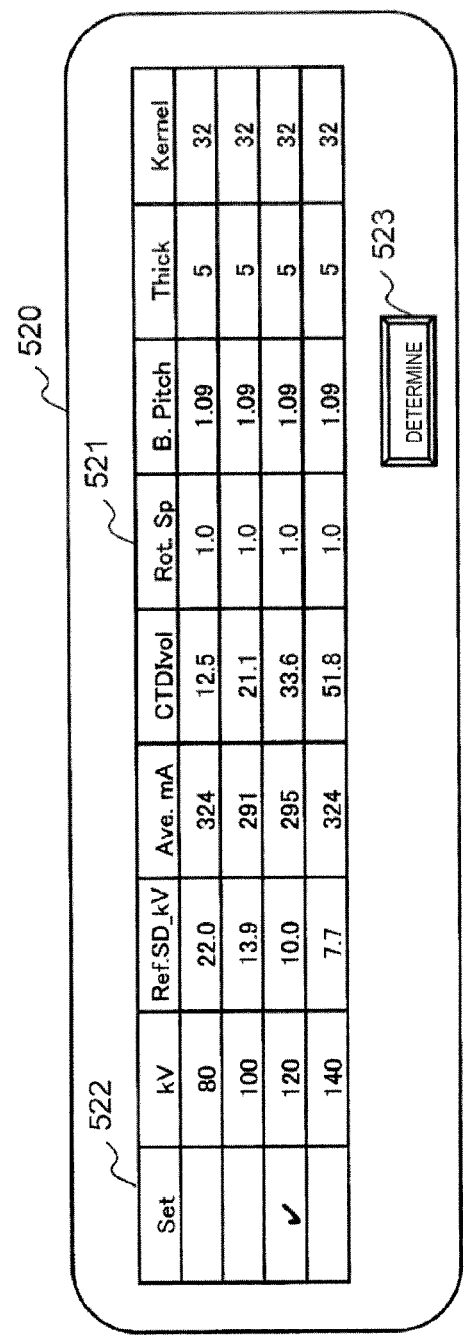
FIG. 6 is an explanatory view for explaining a display example of simultaneous evaluation index display of the second embodiment.

In addition, when the scan index calculation section 480 calculates a scan condition evaluation index at each tube voltage, the calculation result display section 470 generates a simultaneous evaluation index display 520 and displays it on the display device 260. FIG. 6 shows a display example of the simultaneous evaluation index display 520. As shown in this drawing, the simultaneous evaluation index display 520 includes a scan condition evaluation index 521, a selection reception column 522, and a determination button 523 for each tube voltage. Here, a case where four kinds of tube voltages of 80, 100, 120, and 140 can be set in the X-ray CT apparatus 100 is shown as an example.

In the simultaneous evaluation index display 520, not only the scan condition evaluation index calculated by the scan index calculation section 480 but also the scan speed (Rot. Sp), beam pitch (B. Pitch), image slice thickness (Thick), and image reconstruction filter (Kernel) may be displayed in the scan condition evaluation index 521. These parameters are input as imaging conditions by the operator in advance at the time of reference setting, protocol setting, and the like.

The selection reception column (Set) 522 is a region receiving the selection of the operator regarding using which tube voltage when executing a scan. In FIG. 6, a case is illustrated in which 120 kV is selected as a scan tube voltage and highlighted. The determination button 523 receives an instruction to determine the selected tube voltage and the scan condition evaluation index matched with the tube voltage as imaging conditions.

In addition, here, each value of the reference SD (Ref. SD_kV), the scan speed (Rot. Sp), the beam pitch (B. Pitch), the image slice thickness (Thick), and the image reconstruction filter (Kernel) can be changed by the operator. In the simultaneous evaluation index display 520, a value that is directly input in each column is received. That is, when a value is input in a certain column, the scan index calculation section 480 receives the value and calculates the average tube current (Ave. mA) and the amount of exposure (CTDIvol). In this case, when a value is input in the reference SD (Ref. SD_kV) column, the scan index calculation section 480 calculates the reference SD of other tube voltages and then calculates the average tube current (Ave. mA) and the amount of exposure (CTDIvol) on the basis of the new input parameters.

FIG. 7 shows a display example of the simultaneous evaluation index display 520 after a change. FIG. 7 shows an example where the reference SD (Ref. SD_kV) at the scan tube voltage of 100 kV has been changed from 13.9 to 13.0 and the beam pitch (B. Pitch) at the scan tube voltage of 100 kV has been changed from 1.09 to 0.84. This is an example where the change occurs since the operator desires higher quality.

When an instruction to change the value of the reference SD (Ref. SD_kV) is received, the scan index calculation section 480 performs automatic recalculation based on 13.0 for each reference SD (Ref. SD_kV) in the other scan tube voltage conditions. The calculation is performed by substituting 13.0 into Ref. SD_kVptcl and substituting 100 kV into kVptcl in the above-described expression (8).

Figure 8:
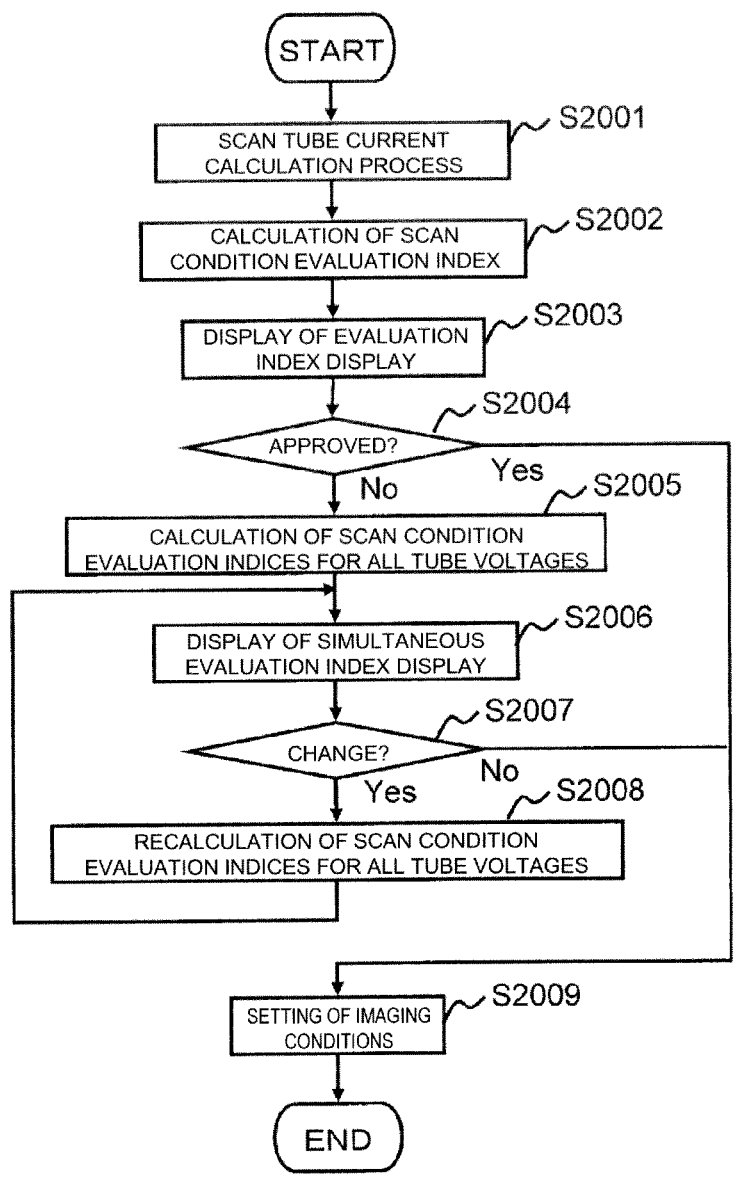
FIG. 8 is a flow chart of the imaging preparation process of the second embodiment.

Hereinafter, the flow of the imaging preparation process by the scan planning unit 281 in the present embodiment will be described. FIG. 8 is a process flow of the imaging preparation process of the present embodiment. Also in the present embodiment, the scan planning unit 281 starts the imaging preparation process in response to an instruction to start the imaging preparation process from the operator. In addition, also in the present embodiment, the standard tube voltage, the standard tube current, and the standard object model are stored in the storage device 250 in advance.

When an instruction to start the imaging preparation process is received, the scan planning unit 281 of the present embodiment executes steps S1001 to S1007 in the imaging preparation process of the first embodiment to calculate a scan tube current at the scan tube voltage (scan tube current calculation processing; step S2001).

Then, the scan index calculation section 480 calculates the scan condition evaluation index of the scan tube voltage (step S2002). The calculation result display section 470 creates the evaluation index display 510 and displays it on the display device 260 (step S2003), and waits for an instruction from the operator.

When an instruction of approval is received from the operator (step S2004), the scan planning unit 281 sets the scan tube voltage and the scan condition evaluation index, which are displayed, as the imaging conditions (step S2009), and ends the process.

On the other hand, when an instruction of simultaneous display is received from the operator (step S2004), the scan index calculation section 480 calculates the above-described scan condition evaluation index for each tube voltage that can be set in the X-ray CT apparatus 100 (step S2005). The calculation result display section 470 creates the simultaneous evaluation index display 520 and displays it on the display device 260 (step S2006), and waits for an instruction from the operator.

When a specific tube voltage is selected and an instruction of determination without a change in the value is received (step S2007), the scan planning unit 281 sets the selected tube voltage and the scan condition evaluation index matched with the tube voltage as the imaging conditions (step S2009), and ends the process.

On the other hand, when an instruction to change the value of the scan condition evaluation index is received from the operator (step S2007), the scan index calculation section 480 recalculates the scan condition evaluation index with the value after a change as a reference (step S2008). Then, the process returns to step S2006 to repeat the processing.

As described above, according to the present embodiment, the input imaging conditions, the calculated tube current, and the reference SD are displayed as imaging conditions evaluation indices, and the operator is made to select the preference. In addition, according to the instruction of the operator, imaging conditions evaluation indices when setting the other tube voltages as the scan tube voltage are simultaneously displaced.

Therefore, the operator can observe the display and perform comparison with other imaging conditions or perform a change to other imaging conditions. Since the present embodiment has such a configuration, it is possible to optimize the amount of exposure and the image quality while appropriately taking into consideration contrast variation in the case of different imaging conditions in addition to the effects obtained in the first embodiment.

In addition, the parameter that the operator inputs as an image quality level can be changed to a desired one. The image quality level after a change is a target image SD that is an upper limit when imaging the standard object with the scan tube voltage. Therefore, not only the difference between the image SD of the obtained image and the input value is small, but also it is possible to obtain an image with image quality closer to the desired image quality.

In addition, in the embodiment described above, limitations on the input value are not set upon changing the value of the reference SD. However, for example, it is possible to set the limitation, such as receiving as an input only the values within ±10% of the reference SD calculated by the method of the first embodiment. In this manner, it is possible to obtain an image with image quality closer to the desired image quality without sacrificing the consideration of contrast. Similar for other parameters that can be changed, changes within a range of the limitations of the apparatus set in advance may be received.

In addition, although the selected scan tube voltage is highlighted in the present embodiment, the present invention is not limited thereto. For example, it is possible to compare the amounts of exposure in conditions of all scan tube voltages that can be selected and to highlight the scan tube voltage condition in which the amount of exposure becomes a minimum.

Third Embodiment

Next, a third embodiment to which the present invention is applied will be described. The present embodiment has basically the same configuration as each of the embodiments described above, but the method of specifying the standard object size is different. That is, in the embodiments described above, the standard object size is calculated from the long-axis length and the short-axis length of the water-equivalent ellipse registered in advance as a standard object model or from the standard body weight and the like registered in advance. In the present embodiment, however, the standard object size is determined by setting the predetermined slice position (reference SD setting line) on the scanogram image. Therefore, a computer apparatus 210 of the present embodiment includes a scan planning unit 282 instead of the scan planning unit 280 of the first embodiment. Hereinafter, the present embodiment will be described focusing on the different configuration from the first embodiment.

Figure 9:
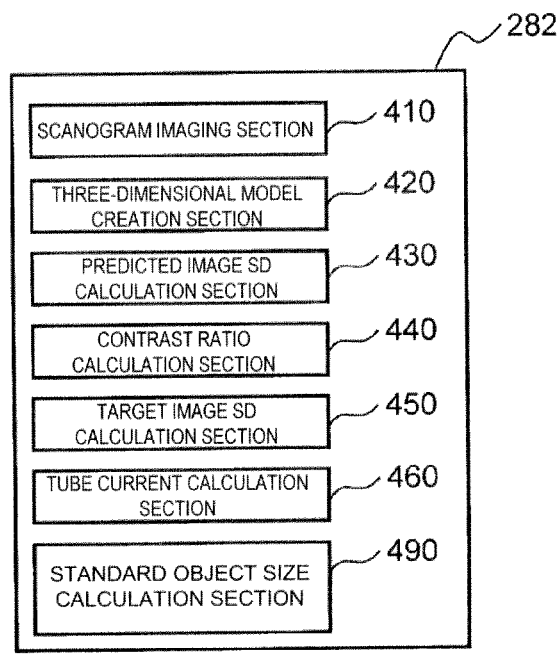
FIG. 9 is a functional block diagram of a scan planning unit of a third embodiment.

FIG. 9 shows a functional block of the scan planning unit 282 of the present embodiment. As shown in this drawing, the scan planning unit 282 of the present embodiment has basically the same configuration as the scan planning unit 280 of the first embodiment, and includes a scanogram imaging section 410, a three-dimensional model creation section 420, a predicted image SD calculation section 430, a contrast ratio calculation section 440, a target image SD calculation section 450, and a tube current calculation section 460. In addition, the scan planning unit 282 of the present embodiment includes a standard object size calculation section 490.

Figure 10:
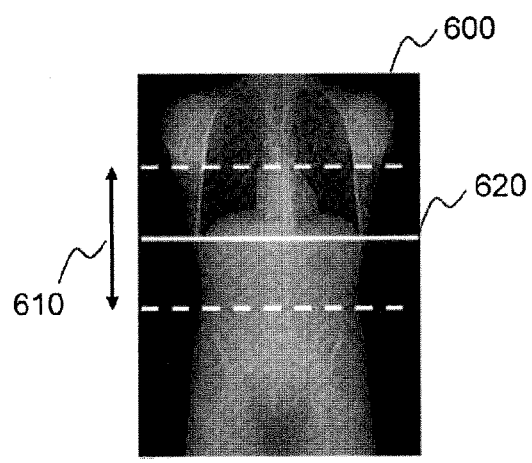
FIG. 10 is an explanatory view for explaining a method of setting the standard reference SD setting line of the third embodiment.

The standard object size calculation section 490 receives the input of the standard reference SD setting line on the scanogram image. A standard reference SD setting line 620 is set within a scan range 610 on a scanogram image 600, as shown in FIG. 10. First, the operator sets the scan range 610 on the scanogram image 600 displayed on the display device 260, and sets the standard reference SD setting line 620 within the set scan range 610. The standard object size calculation section 490 receives the input of the operator and stores it in the storage device 250. Although the standard reference SD setting line 620 is generally set within the scan range 610 herein, the standard reference SD setting line 620 may also be set outside the scan range 610.

In addition, when the three-dimensional model creation section 420 creates a three-dimensional object model, the standard object size calculation section 490 sets an elliptical cross-section of the three-dimensional object model at the Z position corresponding to the standard reference SD setting line 620 as a standard object model. Then, the standard object size (WDia(std)) is calculated from the long-axis length (WDia_X(std)) and the short-axis length (WDia_Y(std)) of the elliptical cross-section using the expression (1) of the first embodiment.

Figure 11:
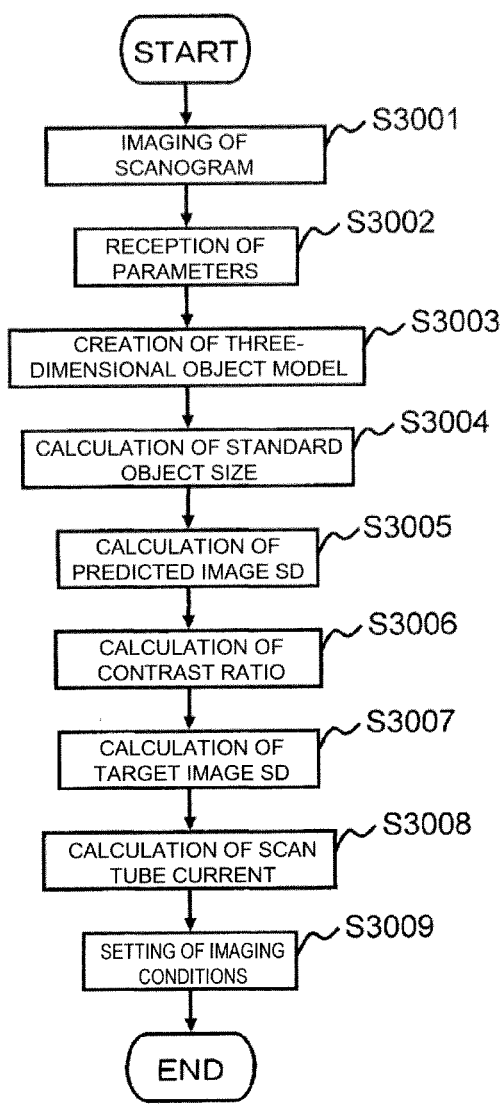
FIG. 11 is a flow chart of the imaging preparation process of the third embodiment.

Hereinafter, the flow of the imaging preparation process by the scan planning unit 282 of the present embodiment will be described. FIG. 11 is a process flow of the imaging preparation process of the present embodiment. Also in the present embodiment, the scan planning unit 282 starts the imaging preparation process in response to an instruction to start the imaging preparation process from the operator. In addition, elliptical data indicating the standard tube voltage, the standard tube current, and the standard object is stored in the storage device 250 in advance.

First, the scanogram imaging section 410 executes scanogram imaging to obtain scanogram data and a scanogram image (step S3001).

Then, the scan planning unit 280 receives the setting of various parameters through the input device 270 (step S3002). Here, in addition to the inputs of the scan range (that is, a scan start position and a scan end position), scan tube voltage, scan time, X-ray collimation conditions, image slice thickness, type of a reconstruction filter function, field-of-view size, and image quality level (standard reference SD), the input of the standard reference SD setting line 620 is received. The scan range 610 and the standard reference SD setting line 620 are received on the scanogram image 600 displayed on the display device 260.

Then, the three-dimensional model creation section 420 creates a three-dimensional object model using the method as in the first embodiment (step S3003).

Then, the standard object size calculation section 470 calculates the standard object size (step S3004). Here, the water-equivalent ellipse of the three-dimensional object model at the Z position corresponding to the standard reference SD setting line 620 input in step S3002 is specified, and the standard object size is calculated using the long-axis length and the short-axis length of the water-equivalent ellipse.

Then, the predicted image SD calculation section 430 calculates the predicted image SD (SD(Z)_pred) at each slice position Z (step S3005).

Then, the contrast ratio calculation section 440 calculates the contrast ratio (Cnt_Ratio(Z)_kV) at each slice position Z at the scan tube voltage (step S3006). In this case, the size calculated in step S3004 is used as the standard object size.

Then, the target image SD calculation section 430 calculates the target image SD (tgt_SD(Z)) using the contrast ratio (Cnt_Ratio(Z)_kV) and the standard reference SD (Ref. SD_kVptcl) (step S3007).

Then, the tube current calculation section 440 calculates a scan tube current i(Z) at each slice position Z using the predicted image SD (SD(Z)_pred) and the target image SD (tgt_SD(Z)) (step S3008).

The scan planning unit 280 sets the scan tube current calculated through the above procedure and the scan parameters received in step S3002 as imaging conditions (step S3009), and ends the imaging preparation process.

As described above, according to the present embodiment, it is possible to obtain the same effects as in the first embodiment. In addition, in the present embodiment, the operator sets the standard object size directly on the scanogram image. Accordingly, it is easy to check the image quality level as a reference in the sequence of actual imaging.

In addition, although the present embodiment has been described on the basis of the first embodiment herein, the present embodiment can be similarly applied to the second embodiment.

Up to now, the present invention has been described through the three embodiments. The technical range of the present invention is not limited to these embodiments. It is apparent to those skilled in the art that various changes and modifications can be made within the range of the technical idea disclosed in this specification, and it should be understood undoubtedly that they also belong to the technical range of the present invention.

REFERENCE SIGNS LIST

100: X-ray CT apparatus
110: scan gantry
120: X-ray tube device
121: X-ray tube
122: X-ray filter
123: compensation filter
130: X-ray detection unit
140: data collection unit
150: high voltage generation unit
160: X-ray tube rotation control unit
170: bed
180: bed movement control unit
190: object
210: computer apparatus
220: bus
230: scan control unit
240: image reconstruction unit
250: storage device
260: display device
270: input device
280: scan planning unit
281: scan planning unit 282: scan planning unit
310: contrast variation curve
410: scanogram imaging section
420: three-dimensional model creation section
430: predicted image SD calculation section
440: contrast ratio calculation section
450: target image SD calculation section
460: tube current calculation section
470: calculation result display section
480: scan index calculation section
490: standard object size calculation section
510: evaluation index display
511: scan condition evaluation index
512: approval button
513: simultaneous display button
520: simultaneous evaluation index display
521: scan condition evaluation index
522: selection reception column
523: determination button
600: scanogram image
610: scan range
620: standard reference SD setting line

The invention claimed is:

1. An X-ray CT apparatus including an X-ray tube that performs X-ray exposure while rotating around an object, an X-ray detector that is disposed opposite the X-ray tube with the object interposed therebetween and detects the amount of X-rays transmitted through the object, an image reconstruction unit configured to reconstruct a tomographic image of the object on the basis of the amount of X-rays detected by the X-ray detector, and a display unit configured to display the tomographic image, the apparatus comprising:
a receiving unit that receives an image noise standard deviation, which is satisfied when imaging is performed by a specific imaging conditions in which a standard object having a predetermined size is imaged with a specific tube voltage, as a standard image quality level;
a scan planning unit that calculates a target image quality level, which is a target image noise standard deviation, using the standard image quality level, calculates a scan tube current to achieve the target image quality level, and sets imaging conditions at the time of actual imaging using the scan tube current; and
a control unit that controls operations of the X-ray tube, the X-ray detector, and the image reconstruction unit according to the set imaging conditions.

2. The X-ray CT apparatus according to claim 1,
wherein the scan planning unit includes:
a contrast determination section that determines contrast at each slice position of the object at a tube voltage at the time of actual imaging;
a contrast ratio calculation section that calculates, as a contrast ratio, contrast at each slice position at the tube voltage at the time of actual imaging with respect to contrast in the specific imaging conditions; and
a target image quality level calculation section that calculates the target image quality level at each slice position using the contrast ratio at each slice position and the standard image quality level, and
the contrast is a CT value difference between a lesion and a surrounding tissue.

3. The X-ray CT apparatus according to claim 2,
wherein the scan planning unit further includes:
a scanogram imaging section that executes scanogram imaging and generates a scanogram age from obtained scanogram data; and a cross-section model generation section that generates an object cross-section model, which is obtained by modeling a water-equivalent ellipse at each slice position of the object, from the scanogram data, and
the contrast determination section calculates a water-equivalent diameter at each slice position of the object from the object cross-section model and determines contrast at each slice position of the object on the basis of contrast variation characteristics specifying a relationship between contrast and a water-equivalent diameter at each tube voltage set in advance.

4. The X-ray CT apparatus according to claim 3,
wherein the contrast variation characteristics are created for each main component of a contrast agent, and
the contrast determination section selects a contrast characteristic according to a main component of a contrast agent used at the time of actual imaging, the contrast determination being performed on the basis of the contrast characteristic.

5. The X-ray CT apparatus according to claim 1,
wherein the specific tube voltage is a standard tube voltage set in advance in the X-ray CT apparatus.

6. The X-ray CT apparatus according to claim 5,
wherein the scan planning unit further includes a condition evaluation index calculation section that calculates, after calculation of the scan tube current, an average value of the scan tube current and the standard image quality level when the specific tube voltage is set as a tube voltage used at the time of actual imaging,
the display unit displays the average value and the standard image quality level, which are calculated by the condition evaluation index calculation section, as condition evaluation indices,
the receiving unit receives an approval or disapproval for the displayed condition evaluation indices, and
the scan planning unit sets imaging conditions at the time of actual imaging using the calculated scan tube current when the condition evaluation indices are approved through the receiving unit.

7. The X-ray CT apparatus according to claim 6,
wherein, when an instruction to disapprove the imaging conditions evaluation indices is received by the receiving unit, the condition evaluation index calculation section calculates the standard image quality level and the average value of the scan tube current, as condition evaluation indices of each tube voltage, for each of other tube voltages that can be set in the X-ray CT apparatus,
whenever condition evaluation indices of each tube voltage are calculated by the condition evaluation index calculation section, the display unit displays the calculated condition evaluation indices simultaneously so as to match the tube voltage,
the receiving unit receives a selection of a tube voltage, which is used in actual imaging, from tube voltages simultaneously displayed, and
the scan planning unit sets imaging conditions at the time of actual imaging using the selected tube voltage and condition evaluation indices matched with the tube voltage.

8. The X-ray CT apparatus according to claim 7,
wherein the receiving unit receives a change in the standard image quality level of the condition evaluation indices simultaneously displayed, and
when the change is received by the receiving unit, the condition evaluation index calculation section calculates the standard image quality level of each tube voltage on the basis of a value after the change.

9. The X-ray CT apparatus according to claim 1,
wherein information specifying a size of the standard object is input through the receiving unit by an operator.

10. The X-ray CT apparatus according to claim 9,
wherein the scan planning unit further includes:
- a scanogram imaging section that executes scanogram imaging and generates a scanogram image from obtained scanogram data;
- a cross-section model generation section that generates an object cross-section model, which is obtained by modeling a water-equivalent ellipse at each slice position of the object, from the scanogram data; and
- a standard object size calculation section that calculates the size of the standard object, the display unit displays the scanogram image,
the receiving unit receives an input of a line specifying the size of the standard object on the scanogram image, and
the standard object size calculation section calculates the size of the standard object from the water-equivalent ellipse of the object cross-section model corresponding to a position of the input line.

11. The X-ray CT apparatus according to claim 1,
wherein the specific tube voltage is a tube voltage set as an imaging condition of actual imaging.

12. A tube current determination method of determining a scan tube current used in imaging of an X-ray CT apparatus, the method comprising:
- an image quality level receiving step of receiving an image noise standard deviation, which specific imaging conditions are within when imaging a standard object having a size set in advance with a specific tube voltage, as a standard image quality level;
- a target image quality level calculation step of calculating a target image quality level, which is a target image noise standard deviation, using the standard image quality level; and
- a tube current determination step of calculating a scan tube current to achieve the calculated target image quality level and determining a tube current, which is used in actual imaging, from the calculated scan tube current.

13. The tube current determination method according to claim 12,
wherein the tube current determination step includes:
- a contrast determination step of determining contrast at each slice position of the object at a tube voltage at the time of actual imaging;
- a contrast ratio calculation step of calculating, as a contrast ratio, contrast at each slice position at the tube voltage at the time of actual imaging with respect to contrast in the specific imaging conditions; and
- a target image quality level calculation step of calculating the target image quality level at each slice position using the contrast ratio at each slice position and the standard image quality level, and the contrast is a CT value difference between a lesion and a surrounding tissue.

14. The tube current determination method according to claim 12,
wherein the tube current determination step includes:
- an approval or disapproval receiving step of calculating and displaying an average value of the calculated scan tube current and the standard image quality level at a tube voltage at the time of actual imaging, as condition evaluation indices, when the scan tube current is calculated and of receiving an approval or disapproval for the calculation result;
- a condition evaluation index calculation step of calculating, when an approval instruction is not received in the approval or disapproval receiving step, the standard image quality level and the average value of the scan tube current, as condition evaluation indices of each tube voltage, for each of other tube voltages that can be set in the X-ray CT apparatus; and
- a selection receiving step of displaying the condition evaluation indices simultaneously whenever the condition evaluation indices are calculated in the condition evaluation index calculation step and receiving a selection, the calculated scan tube current is determined as a tube current at the time of actual imaging when an approval instruction is received in the approval or disapproval receiving step, and a scan tube current when the selected condition evaluation index is calculated is determined as a tube current at the time of actual imaging when the selection is performed in selection receiving step, and in the condition evaluation index calculation step, when a value of the standard image quality level is changed on the simultaneous display, the condition evaluation indices of each tube voltage are recalculated on the basis of a value after the change.

* * * * *